United States Patent [19]

Murray

[11] Patent Number: 4,604,464

[45] Date of Patent: Aug. 5, 1986

[54] IMMUNOMODULATORY 3-(SUBSTITUTED AMINOBENZOYL)-3,4-DIHYDROPH-THALAZIN-1(2H)-ONES

[75] Inventor: Robert J. Murray, Penfield, N.Y.

[73] Assignee: Pennwalt Corporation, Philadelphia, Pa.

[21] Appl. No.: 636,633

[22] Filed: Aug. 1, 1984

[51] Int. Cl.[4] .............................................. C07D 237/30
[52] U.S. Cl. ..................................................... 544/237
[58] Field of Search .......................... 544/237; 424/250; 514/248

[56] References Cited

U.S. PATENT DOCUMENTS 3,882,119 5/1975 Nathanson et al. .................. 424/250
4,382,143 5/1983 Shepherd ............................ 544/332

OTHER PUBLICATIONS

CA 72 55483b.
CA 71 124361d.
CA 75 151821t.

Primary Examiner—Veronica P. Hoke

[57] ABSTRACT

The novel compound, 3-(o-aminobenzoyl)-3,4-dihydrophthalazin-1(2H)-one and novel 3-(substituted aminobenzoyl)-3,4-dihydro-phthalazin-1(2H)-ones, such as 3-(o-methylaminobenzoyl)-3,4-dihydro-phthalazin-1(2H)-one and 3-(o-benzylaminobenzoyl)-3,4-dihydro-phthalazin-1(2H)-one; useful as immunomodulators; and processes for the synthesis of the compounds.

14 Claims, No Drawings

IMMUNOMODULATORY 3-(SUBSTITUTED AMINOBENZOYL)-3,4-DIHYDROPHTHALAZIN-1(2H)-ONES

BACKGROUND OF THE INVENTION

(1) Field of the Invention

This invention pertains to derivatives of 3,4-dihydrophthalazin-1(2H)-one in which that molecule has been substituted in the 3-position with either aminobenzoyl or a substituted aminobenzoyl.

(2) Description of the Prior Art

U.S. Pat. No. 3,882,119 discloses certain derivatives of 3,4-dihydrophthalazin-1(2H)-one and procedures for their synthesis. The disclosed derivatives consist of 3,4-dihydrophthalazin-1(2H)-one substituted in the 3-position with an aminobenzoyl halide (which may itself be substituted) in which the amino group is either para or meta and the halogen is ortho.

In Chemical Abstracts, vol. 72, No. 55483b, and Chemical Abstracts vol. 71, No. 124,361d, the compound, 3-(p-chlorobenzoyl)-3,4-dihydro-1(2H)-phthalazinone, and methods for its synthesis are disclosed.

BRIEF SUMMARY OF THE INVENTION

This invention relates to novel compounds of the formula

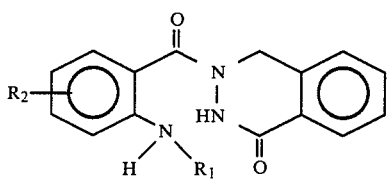

wherein $R_1$ is H, $C_1$–$C_4$ lower alkyl, $C_3$–$C_7$ cycloalkyl, $C_6$–$C_{14}$ aryl, $C_6$–$C_{14}$ substituted aryl, or $C_4$–$C_{13}$ heteroaryl, and $R_2$ is H, $C_1$–$C_4$ lower alkyl, $C_1$–$C_8$ alkoxy, OH, $NH_2$ or $NO_2$.

The invention also relates to a process which comprises reacting 3,4-dihydrophthalazin-1(2H)-one with a compound of the formula

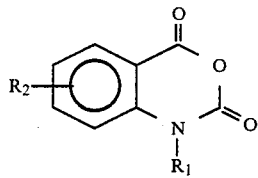

wherein $R_1$ and $R_2$ are defined as above to form a compound of the formula

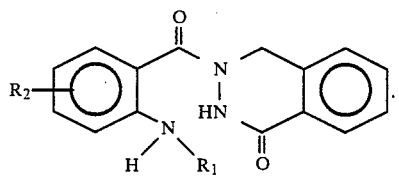

DETAILED DESCRIPTION

Utility

The compounds of this invention are useful as immunomodulators. Immunomodulatory activity has been demonstrated for 3-(o-methylaminobenzoyl)-3,4-dihydrophthalazin-1(2H)-one, 3-(o-benzylaminobenzoyl)-3,4-dihydrophthalazin-1(2H)-one, and 3-(o-aminobenzoyl)-3,4-dihydrophthalazin-1(2H)-one.

Compounds

The compounds of this invention are:

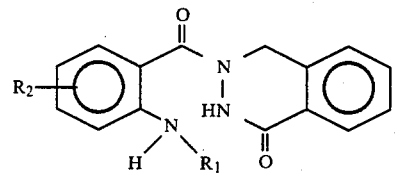

wherein $R_1$ is H, $C_1$–$C_4$ lower alkyl (i.e., lower alkyl group of having one to four carbon atoms), $C_3$–$C_7$ cycloalkyl, $C_6$–$C_{14}$ aryl, $C_6$–$C_{14}$ substituted aryl (including benzyl), or $C_4$–$C_{13}$ heteroaryl, and $R_2$ is H, $C_1$–$C_4$ lower alkyl, $C_1$–$C_8$ alkoxy, OH, $NH_2$ or $NO_2$.

Formation of the Compounds (1) Formation of 3-(Substituted aminobenzoyl)-3,4-dihydrophthalazin-1(2H)-ones The reaction may be summarized as follows:

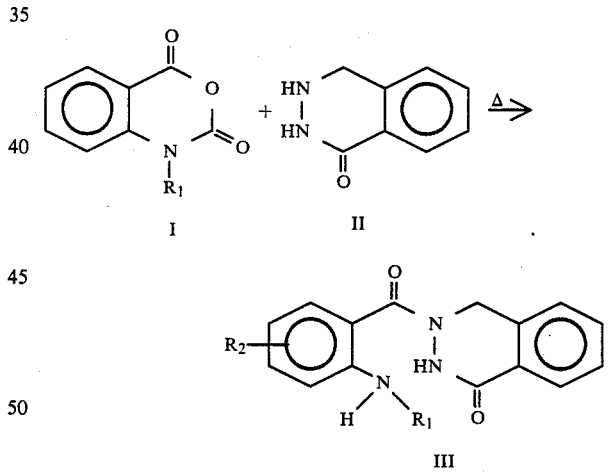

where $R_1$ and $R_2$ are defined as above.

The above reaction is typically accomplished by reacting an N-substituted isatoic anhydride (compound I; prepared from isatoic anhydride by procedures described in G. E. Hardtmann et al, J. of Heterocyclic Chemistry, Vol. 12, p 565–572 (1975)) with an equivalent amount of 3,4-dihydrophthalazin-1(2H)-one (compound II) in an aprotic solvent such as toluene or xylene at elevated temperatures, preferably in the range from 100° C. to 145° C. The above reaction can also be performed in a polar solvent, such as dimethyl formamide, in which case a range of 70° C. to 90° C. is preferred. Depending on the solvent and the nature of compounds I and II, the time of the reaction is varied from 4 to 24 hours. The preferred reaction time is 16 hours. The product, 3-(substituted aminobenzoyl)-3,4-dihydrophthalazin-1(2H)-one (compound III), forms a precipitate when the mixture is cooled to room temperature. The preceipitate may be washed with the aprotic solvent at room temperature.

(2) Formation of 3-(aminobenzoyl)-3,4-dihydrophthalazin-1(2H)-one

Two grams of the catalyst, 10% Pd/C, is added to a suspension of 7.2 g of 3-(o-benzoylaminobenzyl)-3,4-dihydrophthalazin-1(2H)-one in 1 liter of ethanol and the mixture is hydrogenated in a Paar apparatus for 16 hours. The catalyst is filtered off and the filtrate is evaporated to afford the product, 3-(o-aminobenzoyl)-l3,4-dihydro-phthalazin-1(2H)-one, as a colorless solid. Recrystallization from ethanol affords the product as a colorless powder.

ILLUSTRATIVE EXAMPLES

Example 1

Preparation of
3-(o-Methylaminobenzoyl)-3,4-dihydro-phthalazin-1(2H)-one

To 3.3 g (0.022 ml) of 3,4-dihydro-phthalazin-1(2H)-one dissolved in 100 ml of xylene was added 3.9 g (0.022 mol) of N-methylisatoic anhydride and the solution was stirred and heated at reflux under $N_2$ for 16 hours. The mixture was then cooled to room temperature (about 25° C.) whereupon a heavy precipitate formed. The 3-(o-methylaminobenzoyl)-3,4-dihydro-phthalazin-1(2H)-one was collected as a solid, washed well with xylene to give an off-white powder, mp 199°–202° C.

Anal. Calcd. for $C_{16}H_{15}N_3O_2$: C, 68.31; H, 5.37; N, 14.93. Found: C, 68.27; H, 5.35; N, 14.75.

Immunoregulatory activity of the compound, 3-(o-methylaminobenzoyl-3,4-dihydro-phthalazin-1(2H)-one, was assessed by the Kennedy plaque assay [J. C. Kennedy et al, *Immunol.*, 20, 253 (1971)]. In the assay, the change in the number of plaques is a direct correlate of the number of antibody secreting cells in the test animal's spleen. The results obtained were:

| Dose of the Compound (mg/kg) | Percent change in the number of plaques |
| --- | --- |
| 1.56 | −32 |
| 6.25 | −45 |
| 25 | −35 |

EXAMPLE 2

Preparation of
3-(o-Benzylaminobenzoyl)-3,4-dihydro-phthalazin-1(2H)-one 3,4-Dihydrophthalazin-1(2H)-one was reacted with N-benzylisatoic anhydride according to the general procedure above to produce 3-(o-benzylaminobenzoyl)-3,4-dihydrophthalazin-1(2H)-one as a colorless solid, mp 206°–208° C.

Anal. Calc. for $C_{22}H_{19}N_3O_2$: C, 73.93; H, 5.36; N, 11.76. Found: C, 73.91; H, 5.34; N, 11.63.

Immunoregulatory activity of the compound, 3-(o-benzylaminobenzoyl)-3,4-dihydro-phthalazin-1(2H)-one was assessed by the Kennedy Plaque Assay referred to in Example 1. The results obtained were:

| Dose of the Compound (mg/kg) | Percent change in the number of plaques |
| --- | --- |
| 6.25 | +30 |
| 25 | −32 |

Example 3

Preparation of
3-(o-Aminobenzoyl)-3,4-dihydro-phthalazin-1(2H)-one

To 7.2 g of 3-(o-benzylaminobenzoyl)-3,4-dihydrophthalazin-1(2H)-one suspended in 1 liter of EtOH was added 2 g of 10% Pd/C and the mixture was hydrogenated in a Paar apparatus for 16 hours. The catalyst was filtered off and the filtrate evaporated to afford 5.0 g of a colorless solid. Recrystallization from aqueous EtOH afforded 3-(o-amino-benzoyl)-3,4-dihydro-phthalazin-1(2H)-one as a colorless powder in 62% yield; mp 156°–157° C.

Anal. Calc. for $C_{15}H_{13}N_3O_2$: C, 67.40; H, 4.90; N, 15.72. Found: C, 67.22; H, 4.90; N, 15.67.

Immunoregulatory activity of the compound, 3-(o-aminobenzoyl)-3,4-dihydro-phthalazin-1(2H)-one was assessed by the Kennedy Plaque Assay referred to in Example 1. The results obtained were:

| Dose of the Compound (mg/kg) | Percent change in the number of plaques |
| --- | --- |
| 1.56 | −18 |
| 25 | +10 |

ADDITIONAL ILLUSTRATIONS OF COMPOUNDS INCLUDED IN THE INVENTION

By following the procedure of Example 1, using the following N-substituted isatoic anhydrides in place of N-methylisatoic anhydride:
N-ethylisatoic anhydride,
N-isopropylisatoic anhydride,
N-butylisatoic anhydride,
N-cyclohexylisatoic anhydride,
N-(2,3-dimethylphenyl)isatoic anhydride,
N-(3-trifluoromethyl)isatoic anhydride,
N-phenylisatoic anhydride, the products are, respectively:
3-(o-ethylaminobenzoyl)-3,4-dihydrophthalazin-1(2H)-one,
3-(o-isopropylaminobenzoyl)-3,4-dihydrophthalazin-1(2H)-one,
3-(o-butylaminobenzoyl)-3,4-dihydrophthalazin-1(2H)-one,
3-(o-cyclohexylaminobenzoyl)-3,4-dihydrophthalazin-1(2H)-one,
3-[2,3-dimethylphenylamino)benzoyl]-3,4-dihydrophthalazin-1(2H)-one,
3-[o-(3-trifluoromethylphenylamino)benzoyl]3,4-dihydrophthalazin-1(2H)-one, and
3-(o-phenylaminobenzoyl)-3,4-dihydrophthalazin-1(2H)-one.

The above list is not intended to limit the scope of the invention but is included for illustrative purposes only.

What is claimed is:
1. A compound of the formula

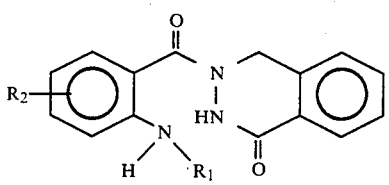

wherein
  $R_1$ is H, $C_1$–$C_4$ lower alkyl, $C_3$–$C_7$ cycloalkyl, $C_6$–$C_{14}$ aryl, benzyl, or $C_6$–$C_{14}$ aryl monosubstituted with or disubstituted with either methyl or trifluoromethyl, and
  $R_2$ is H, $C_1$–$C_4$ lower alkyl, $C_1$–$C_8$ alkoxy, OH, $NH_2$ or $NO_2$.

2. The compound as defined in claim 1 wherein $R_1$ is methyl and $R_2$ is H.

3. THe compound as defined in claim 1 wherein $R_1$ is benzyl and $R_2$ is H.

4. The compound as defined in claim 1 wherein $R_1$ is H and $R_2$ is H.

5. The compound as defined in claim 1 wherein $R_1$ is ethyl and $R_2$ is H.

6. The compound as defined in claim 1 wherein $R_1$ is isopropyl and $R_2$ is H.

7. The compound as defined in claim 1 wherein $R_1$ is butyl and $R_2$ is H.

8. The compound as defined in claim 1 wherein $R_1$ is cyclohexyl and $R_2$ is H.

9. The compound as defined in claim 1 wherein $R_1$ is 2,3-dimethylphenyl and $R_2$ is H.

10. The compound as defined in claim 1 wherein $R_1$ is 3-trifluoromethylphenyl and $R_2$ is H.

11. The compound as defined in claim 1 wherein $R_1$ is phenyl and $R_2$ is H.

12. The compound as defined in claim 1 wherein $R_1$ is H, $C_1$–$C_4$ lower alkyl, $C_3$–$C_7$ cycloalkyl, $C_6$–$C_{14}$ aryl, benzyl or $C_6$–$C_{14}$ aryl monosubstituted with or disubstituted with either methyl or trifluoromethyl, and $R_2$ is H, $C_1$–$C_4$ lower alkyl, $C_1$–$C_8$ alkoxy, OH, $NH_2$ or $NO_2$.

13. The compound as defined in claim 1 wherein $R_1$ is H, $C_1$–$C_4$ lower alkyl, $C_3$–$C_7$ cycloalkyl, or $C_6$–$C_{14}$ aryl, and $R_2$ is H, $C_1$–$C_4$ lower alkyl, $C_1$–$C_8$ alkoxy, OH, $NH_2$ or $NO_2$.

14. A process for forming a compound of the formula

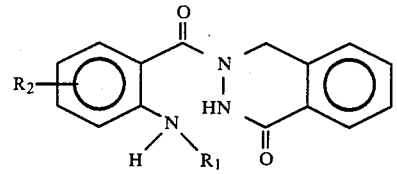

which comprises reacting a compound of the formula

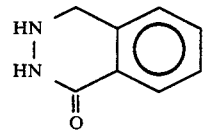

with a compound of the formula

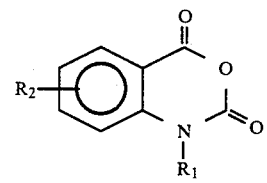

wherein
  $R_1$ is H, $C_1$–$C_4$ lower alkyl, $C_3$–$C_7$ cycloalkyl, $C_6$–$C_{14}$ aryl, benzyl, or $C_6$–$C_{14}$ aryl monosubstituted with or disubstituted with either methyl or trifluoromethyl, and
  $R_2$ is H, $C_1$–$C_4$ lower alkyl, $C_1$–$C_8$ alkoxy, OH, $NH_2$ or $NO_2$.

* * * * *